United States Patent [19]

Gaborski et al.

[11] Patent Number: 5,426,684
[45] Date of Patent: Jun. 20, 1995

[54] TECHNIQUE FOR FINDING THE HISTOGRAM REGION OF INTEREST FOR IMPROVED TONE SCALE REPRODUCTION OF DIGITAL RADIOGRAPHIC IMAGES

[75] Inventors: Roger S. Gaborski, Pittsford; Lori L. Barski, Mendon, both of N.Y.

[73] Assignee: Eastman Kodak Company, Rochester, N.Y.

[21] Appl. No.: 152,772

[22] Filed: Nov. 15, 1993

[51] Int. Cl.⁶ .......................................... G01N 23/04
[52] U.S. Cl. ...................................... 378/62; 378/98; 378/901; 395/924; 364/413.13
[58] Field of Search ...................... 364/413.13, 413.23; 395/130, 924; 378/62, 87, 98, 901

[56] References Cited

U.S. PATENT DOCUMENTS

| | | |
|---|---|---|
| 31,847 | 3/1885 | Luckey . |
| 4,839,807 | 6/1989 | Doi et al. ................. 364/413.13 |
| 4,914,295 | 4/1990 | Shimura et al. ............... 250/327.2 |
| 4,914,589 | 4/1990 | Crawford ................... 364/43.17 |
| 4,952,805 | 8/1990 | Tanaka ...................... 250/327.2 |
| 5,040,225 | 8/1991 | Gouge ............................. 382/6 |
| 5,048,097 | 9/1991 | Gaborski et al. ................ 382/14 |
| 5,068,788 | 11/1991 | Goodenough et al. ......... 364/413.14 |
| 5,107,529 | 4/1992 | Boone ........................... 378/157 |
| 5,153,926 | 10/1992 | Jansson et al. .................. 382/54 |
| 5,164,993 | 11/1992 | Capozzi et al. ..................... 382/6 |
| 5,198,669 | 3/1993 | Namiki et al. ................. 290/327.2 |
| 5,331,550 | 7/1994 | Staffore et al. .............. 364/413.02 |

OTHER PUBLICATIONS

Moallemi, "Classifying Cells for Cancer Diagnosis Using Neural Networks," *IEEE Expert.*, 1991, pp. 8–12.
Peter G. Anderson, Linear Pixel Shuffling for Image Processing, an Introduction, Journal of Electronic Imaging, (2), Apr. 1993, pp. 147–154.
Pratt, W., *Digital Image Processing*, Wiley, New York, 1993, pp. 275–284.
Haralick, R., Shanmugam, K., Dinstein, I., Textural Features for Image Classification, *IEEE Trans. Syst. Man. Cyber.*, (SMC-3), Nov. 1973, pp. 141–152.
Haralick, R., Statistical and Structural Approaches to Texture, *Proc. of IEEE*, (67), May 1979, pp. 786–804.

*Primary Examiner*—Paul M. Dzierzynski
*Assistant Examiner*—David Vernon Bruce
*Attorney, Agent, or Firm*—William F. Noval

[57] ABSTRACT

An image processing technique especially useful in processing digital radiographic images. A method for finding a histogram region of interest for improved tone scale reproduction of digital radiographic images includes the following steps. A digital radiographic image is randomly sampled with a sample having an appropriate size to delineate an object of interest. Each sample is processed using texture analysis techniques to extract a plurality of texture features. Using the extracted texture features, each sample is classified with a previously trained neural network classifier to determine its class. Last, the pixel values belonging to the same class are accumulated to form separate histograms for each class. Each of the histograms are then used to optimize tone scale reproduction.

9 Claims, 13 Drawing Sheets

TECHNIQUE FOR FINDING THE HISTOGRAM REGION OF INTEREST FOR IMPROVED TONE SCALE REPRODUCTION OF DIGITAL RADIOGRAPHIC IMAGES

FIELD OF THE INVENTION

This invention relates in general to digital image processing and more particularly to a technique for finding the histogram region of interest for improved tone scale reproduction of digital radiographic images.

BACKGROUND OF THE INVENTION

In medical imaging, accurate diagnosis depends on the detection of small, low contrast details within the image. The probability of detection of these details, in turn, depends critically on their visibility in the image. A number of factors, including the object (body part) being imaged, the exposure geometry and technique, and the characteristics of the detector can affect this visibility.

In conventional screen/film radiography, for example, the output tonescale (i.e. tone reproduction function) is generally already designed into the film by the film manufacturer, and a variety of different films are available to get different "looks" depending on exam types, exposing techniques, and observer preference. In computed radiography (CR) (as described in U.S. Pat. No. Re. 31,847, reissued Mar. 12, 1985, inventor Luckey), on the other hand, the separation of image acquisition and display stages allows an image or portion of an image to be displayed at an arbitrary output contrast depending on the particular need. The ability in CR systems to adjust this output tonescale in a computer before the final image is displayed is one of the powerful features of such systems. However, choosing or creating the appropriate tonescale is not always a simple operation because it depends on, among other things, the exam type, exposure conditions, imaging modality, noise sensitivity of the image acquisition device, and dynamic range of the output device.

Commercially available computed radiography systems typically include an edge enhancement stage and then a tonescale stage. The purpose of tone scale is to define an appropriate transformation function that maps the important image information to the maximum dynamic range of the display medium (either film or soft copy, i.e., CRT display). Various methods have been proposed to generate tonescale curves for CR images. In particular, the histogram-based tonescale transformation is one of the most commonly used techniques for enhancing such images because of its efficiency. The following are exemplary of histogram-based imaging techniques for processing digital medical images: U.S. Pat. Nos. 5,068,788, issued Nov. 26, 1991, inventors Goodenough et al.; 5,198,669, issued Mar. 3, 1993, inventors Namiki, et al.; 4,839,807, issued Jun. 13, 1989, inventor Doi et al.; 5,040,225, issued Aug. 13, 1991, inventor Gouge; 4,914,295, issued Apr. 3, 1990, inventors Shimura et al.; 4,952,805, issued Aug. 28, 1990, inventor Tanaka.

Generally, such histogram-based methods work best when the peak(s) in the histogram corresponding to the undesired regions are far enough away from the peak(s) corresponding to the desired regions that they can be identified as separate. However, if the peaks overlap, which can occur if the undesired regions are nonuniformly illuminated across the image, or if scatter behind the collimators causes the signal level in that area to come close to the highly x-ray absorbing structures in the object (body part), then it becomes more difficult to separate the desired and undesired regions. Consequently, a tonescale transformation will be suboptimum if it is unduly influenced by the undesired regions of the image.

It has been proposed, in the field of digital projection radiography, to present an optimal image for viewing by a radiologist through the use of image processing techniques tying together spatial image segmentation (i.e., body part finding) and histogram analysis. (See: U.S. Pat. No. 5,164,993, issued Nov. 17, 1992, inventors Capozzi and Schaetzing; U.S. patent application Ser. No. 906,191, filed Jun. 29, 1992, inventors Jang and Schaetzing.) These techniques require that the body part be segmented from the foreground and the background and that a rule-based histogram analysis finds the appropriate histogram region of interest that corresponds to the anatomical region being imaged.

There is thus a problem in the prior art of digital radiographic imaging of providing digital image processing techniques which map the important image information to the maximum dynamic range of the display medium, and which facilitate a more accurate analysis of the image histogram.

SUMMARY OF THE INVENTION

According to the present invention, there is provided a solution to the aforementioned problems of the prior art. According to an aspect of the present invention there is provided a method of finding a histogram region of interest for improved tone scale reproduction of digital radiographic images comprising the steps of:

pseudo-randomly sampling a digital radiographic image with a sample having an appropriate size to delineate an region of interest;

processing each sample using texture analysis techniques to extract a plurality of texture features;

using the extracted texture features, classifying said sample with a previously trained neural network classifier to determine its class; and accumulating pixel values belonging to the same class to form separate histograms for each said class, wherein each said histograms can be used to optimize tone scale reproduction.

DESCRIPTION OF THE PREFERRED EMBODIMENTS

Figures 1, 2:
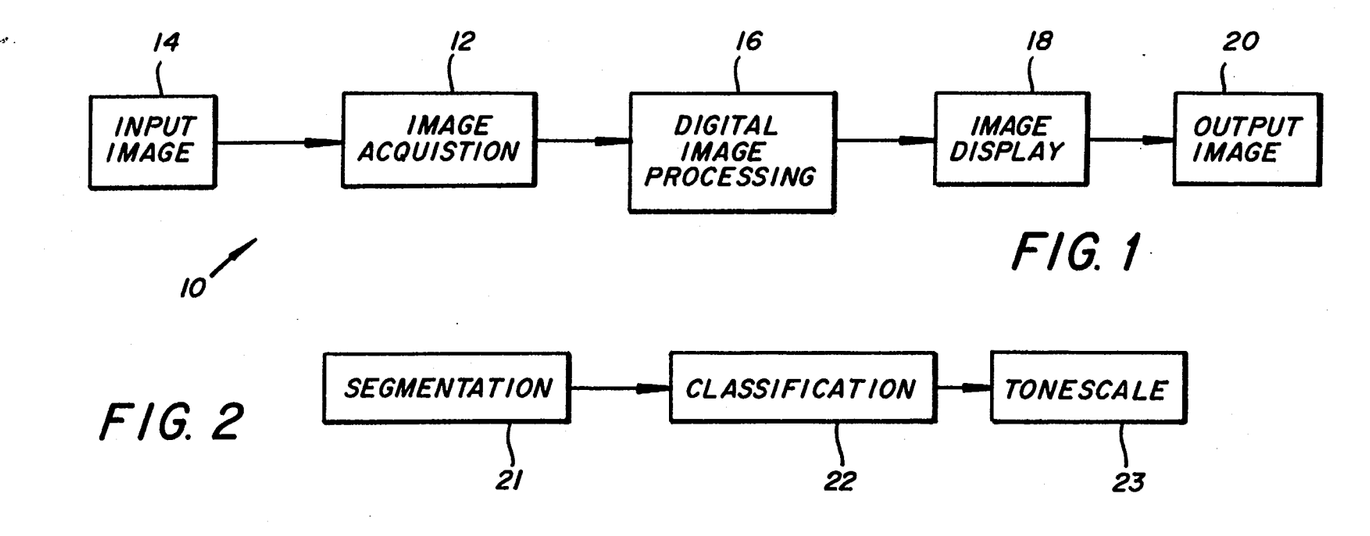
FIG. 1 is a block diagram of an imaging system in which the present invention may be used.
FIG. 2 is a block diagram of an embodiment of the present invention used in image processing of digital radiographic images.

FIG. 1 illustrates a typical system 10 in which the present invention can be practiced. The system consists of an image acquisition section (scanner) 12 in which an input image 14 is converted into a digital radiographic image. A digital image processing section 16 manipulates the digital image signal with image processing algorithms intended to improve the appearance, diagnostic quality, and other properties of the image. The digital image processing section can be a digital computer having known components, such as a digital processing computing device, memory, input and output devices, etc. The processed output image 20 is viewed on image display 18. The digital radiographic image signals to be processed with this invention can be acquired in a variety of different systems, for example, from storage phosphor (computed radiography) systems, film digitizer systems, image intensifier systems, etc. In addition, one can use images acquired from diagnostic imaging scanners, for example, computed tomography (CT), magnetic resonance imaging (MRI), ultrasound (US). For display devices, the most common are film writers (laser printer, cathode ray tube printer) and soft display on a video monitor.

According to the present invention, there is provided an image classification technique to improve the image processing algorithms described in U.S. Pat. No. 5,164,993, issued Nov. 17, 1992, inventors Capozzi and Schaetzing; U.S. patent application Ser. No. 906,191, filed Jun. 29, 1992, inventors Jang and Schaetzing. Preferably the technique of the present invention is used after a digital radiographic image has been segmented according to the algorithm disclosed in the Jang and Schaetzing application. After the classification technique of the present invention is effected, the digital radiographic image is processed with the tone scale algorithms disclosed in U.S. Pat. No. 5,164,993. (FIG. 2, blocks 21, 22, 23).

Figure 3:
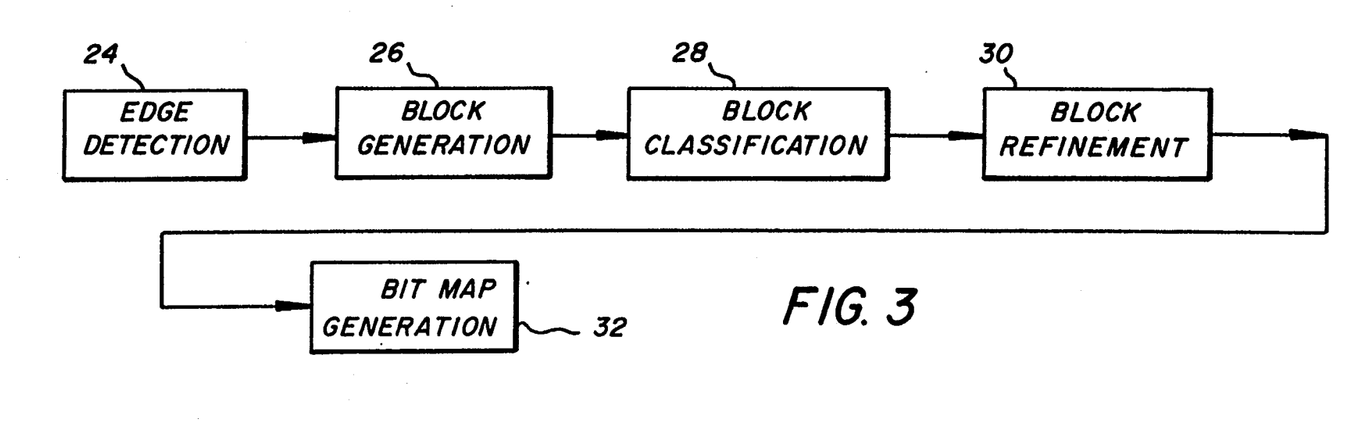
FIG. 3 is a block diagram of a preferred image segmentation procedure.

The segmentation algorithm of Jang and Schaetzing is more clearly illustrated with reference to FIG. 3. The referenced application is referred to for a more complete description of the segmentation technique disclosed. The segmentation method in general, detects and distinguishes in CR images both the regions of the direct x-ray exposure around the body part being imaged (background), and the regions in which beam-limiting devices have been used to restrict the size of the irradiation field (foreground). As shown in FIG. 3, segmentation consists of five steps: edge detection 24, block generation 26, block classification 28, block refinement 30, and bit map generation 32.

The edge detection step 24 can use a variety of edge detection algorithms. However, a morphological edge detector is preferred because of its low sensitivity to noise, its ability to yield an edge strength measure that is proportional to the contrast between the foreground/background and the object, and its efficient implementation. The output of the edge detection step is an edge strength map containing high-amplitude pixels in areas of strong edges and low-amplitude pixels in areas of little or no edge density. Thus, the local edge content is one indicator of the level of detail in various parts of the image, and, therefore, an indicator of whether these parts are more likely to belong to the foreground/background region or to the object.

After the edge detection step, in the block generation step 26, the image is broken into a set of nonoverlapping, contiguous blocks of pixels. Further analysis of the image and the classification into foreground, background, and object take place on a block-by-block basis.

The block classification and block refinement steps 28, 30 are performed next. There are ten possible states each block can have, depending on whether the block is basically homogeneous (relatively low edge density) or nonhomogeneous (relatively high edge density), and what it contains (foreground pixels, background pixels, object pixels, mixtures of foreground and/or background pixels with object pixels). The information about edge content along with similar information from neighboring blocks is fed into a syntactic reasoning section that uses a set of clinically and empirically determined decision rules to classify each block of the image into one of two categories: foreground/background or object. For blocks that are around the periphery of the object, the block refinement step reclassifies portions of the block into the latter two categories. The bit-map generation step 32 creates a two-valued (binary) image that functions as a template which is used in a preferred embodiment of the technique of the present invention.

In general, the technique of the present invention facilitates an accurate analysis of an image histogram by estimating what regions of the histogram correspond to bone, soft tissue, background and foreground based upon texture attributes. With such knowledge, it becomes possible, for example, to allow for more contrast in the bone region at the expense of contrast in the soft tissue region.

Figure 4:
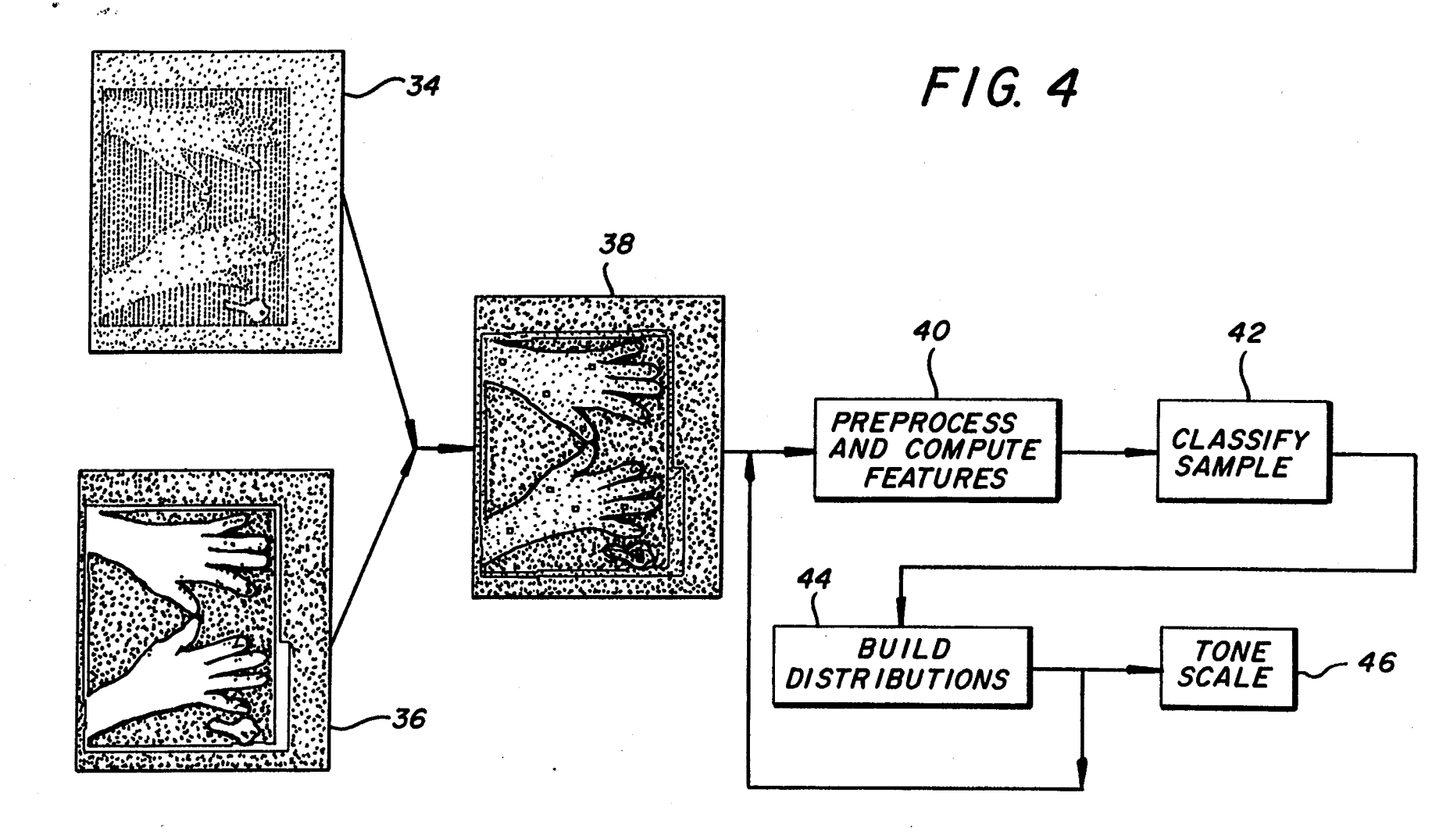
FIG. 4 is a partially diagrammatic, partially block diagram of a preferred embodiment of the present invention.

Referring now to FIG. 4, there is shown a diagrammatic/block diagram illustrating a preferred embodiment of the present invention. As shown, diagram 34 depicts an original radiographic image including background, foreground, and region of interest. Diagram 36 depicts the binary image resulting from the segmentation processing described above. According to the image processing technique of the present invention, the delineated region of interest (the hands), are randomly sampled as illustrated in diagram 38. Each sample is preprocessed and texture features are extracted (box 40). The sample is then classified (box 42) using the features extracted by means of a neural classification technique, as to type, i.e., bone, tissue, background, or foreground. Pixel values corresponding to the same class are accumulated (box 44) to form separate histogram estimates for bone, tissue, background, foreground. These histogram estimates can then be used (box 46) to optimize the tone scale algorithm for bone regions or tissue regions to enhance display of these regions for viewing and diagnosis.

Figure 5:
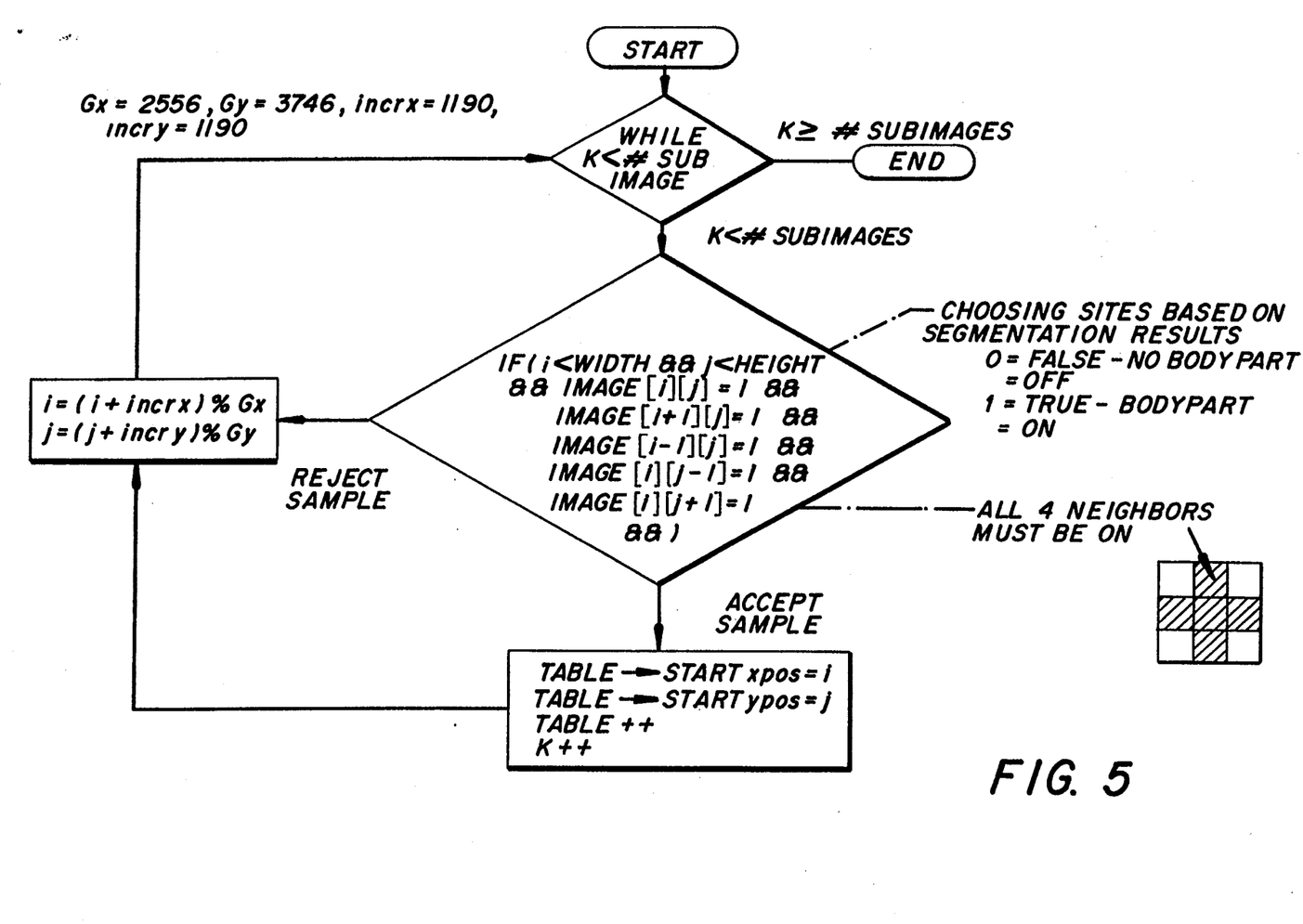
FIG. 5 is a flow chart of image samples processing routine.

The steps of the present invention will now be described in greater detail. The random sampling step of box 38 (FIG. 4) is carried out by extracting subregions of pixels (e.g., 39×39 pixel subregions) from the segmented body part (which may, for example, have a digital value of 12 bits per pixel). The sampling technique preferably is a linear pixel shuffling technique as described in the article of Peter G. Anderson, *Linear Pixel Shuffling for Image Processing, an Introduction, Journal of Electronic Imaging*, (2), April, 1993, Pages 147-154. An exemplary software routine is shown in FIG. 5.

Figure 6:
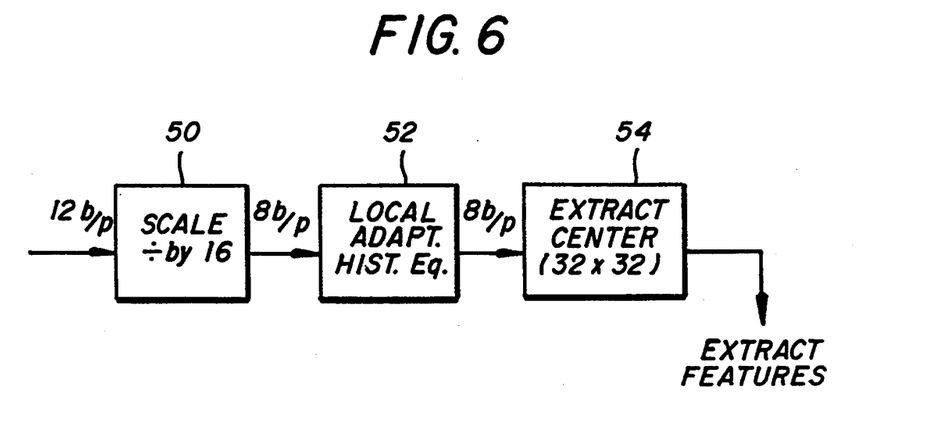
FIG. 6 is a block diagram illustrating the image sample preprocessing steps.
Figure 7:
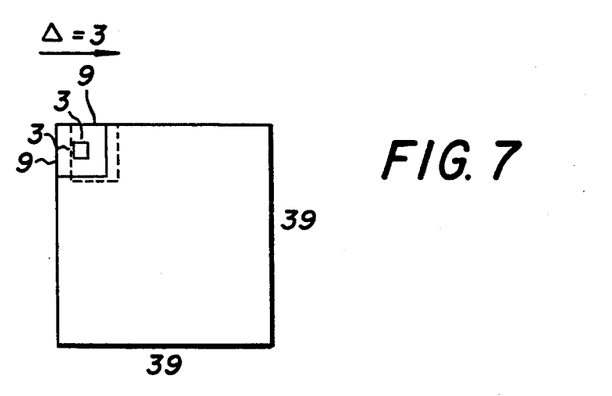
FIG. 7 is a diagrammatic view depicting local adaptive histogram equalization.
Figure 8:
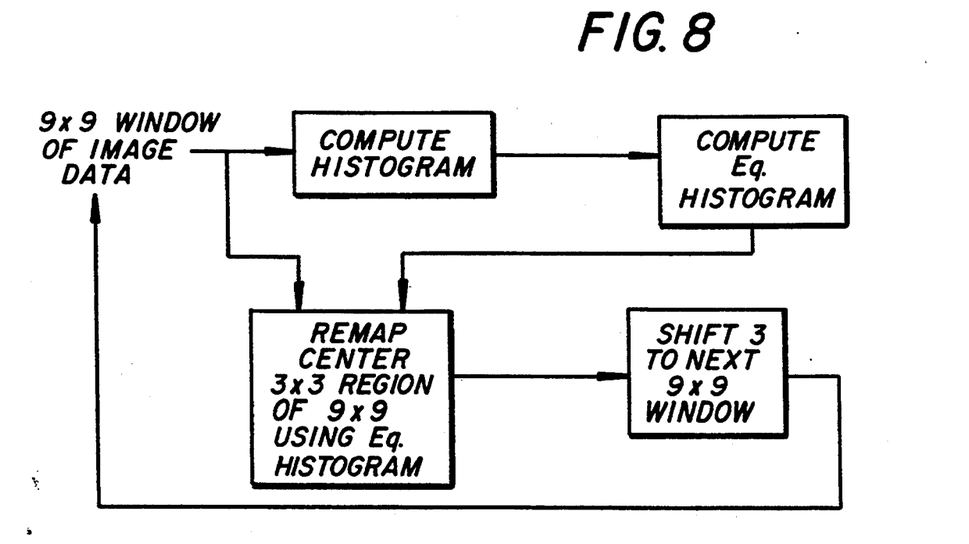
FIG. 8 is a flow chart useful in carrying out the preprocessing steps of FIGS. 6 and 7.
Figures 9, 10, 11:
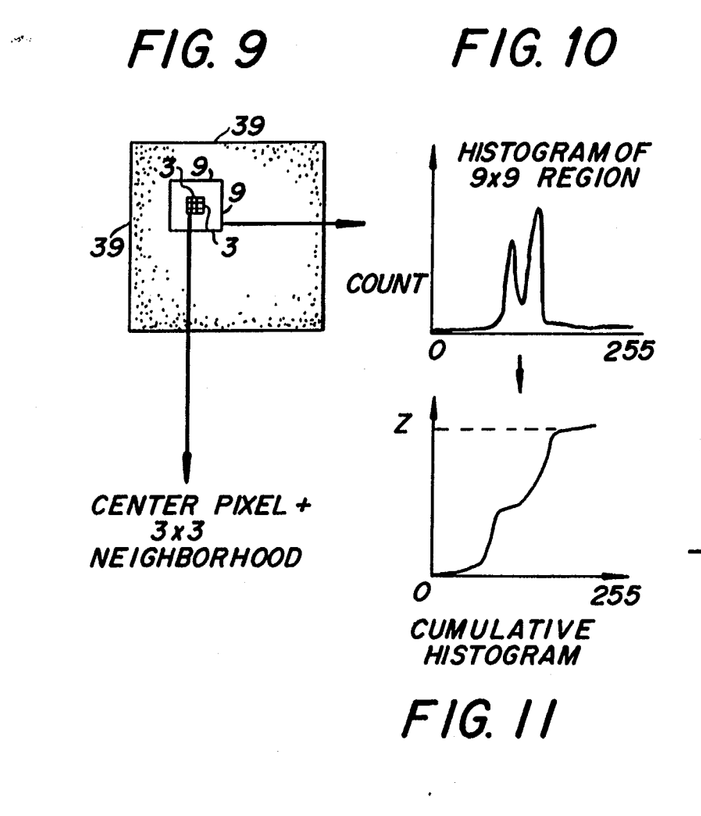
FIGS. 9-14 are graphical views useful in describing the technique of the present invention.
Figure 12:
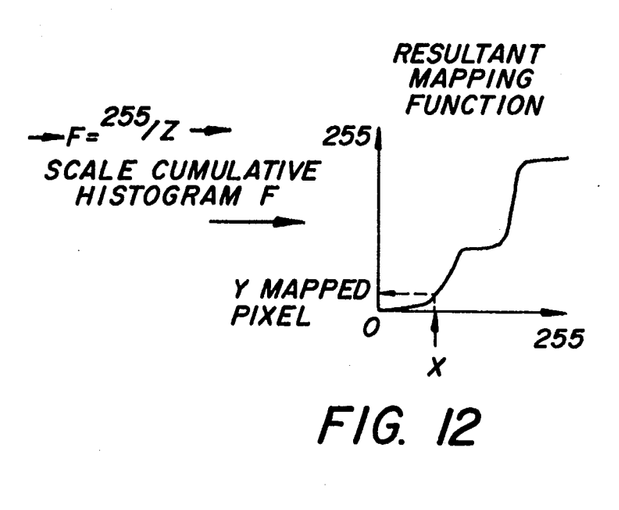
Figure 13:
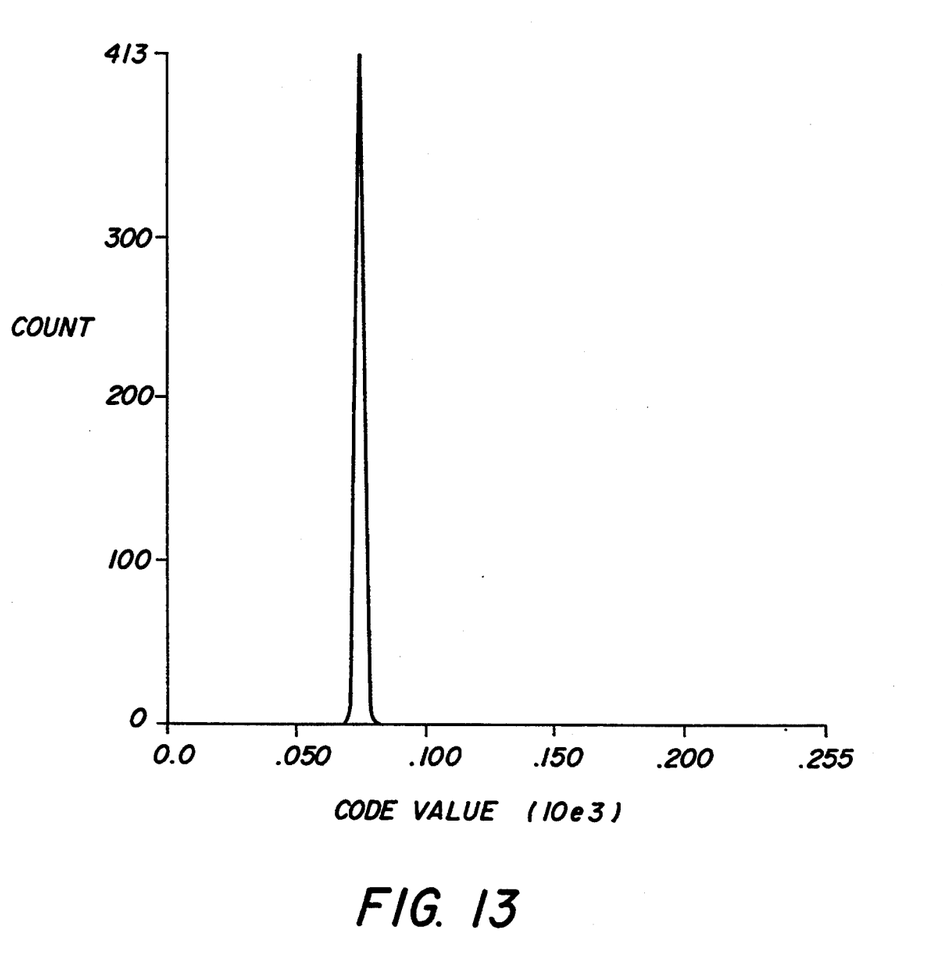
Figure 14:
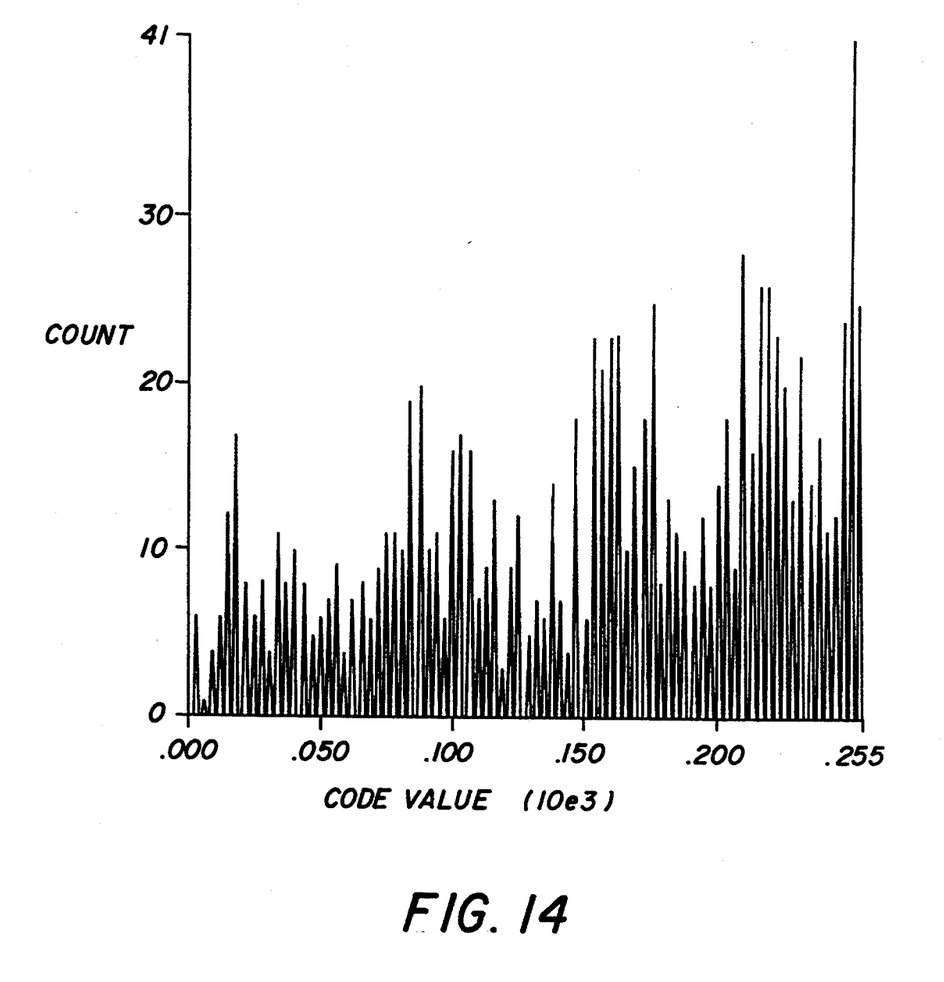

The preprocessing and texture extraction steps of box 40 in FIG. 4 will be described in greater detail with respect to FIGS. 6-15. As shown in FIG. 6, the first preprocessing step 50 reduces the data for each sample by a factor (such as 16). As an example, each 12 bit pixel in a sample is reduced to an 8 bit pixel. A local adaptive histogram equalization process is then performed on each reduced sample. An exemplary technique is described in Pratt, W., (1993), *Digital Image Processing*, Wiley, N.Y., Pages 275-284. As an example, at each 9×9 window position, a histogram is computed (the frequency table of pixel code values). (FIGS. 7, 9, 10) Then an equalization histogram is computed as a cumulative frequency table based on the histogram. Then the center 3×3 pixel region is remapped based on the equalization histogram. (See FIGS. 11,12). The process is repeated at successive windows after shifting by 3 pixels. (FIGS. 7, 9, 10). A software routine of the process is shown in FIG. 8. Thereafter, the middle region (e.g., 32×32 pixels) of each sample is taken (FIG. 6, box 54). FIGS. 13 and 14 respectively illustrate a bone sample histogram before and after local adaptive histogram equalization.

The next step in the process is a feature extraction stage. The texture of an object or an image can be described by adjectives such as random, periodic, smooth, coarse, rough, etc. and can be represented using statistical or structural techniques. Orthopedic bones have unique textural attributes because of trabecular structures in the spongy bone that form reinforcement struts that follow the lines of stress. The radiographic imaging process records these attributes, resulting in a unique texture compared to tissue, background, or foreground. In a preferred embodiment of the invention, two statistical methods of texture analysis are used, gray-level co-occurrence (GLC) matrix (See: Haralick, R., Shanmugam, K., Dinstein, I., (1973), Textural Features for Image Classification, *IEEE Trans. Syst. Man. Cyber.*, (SMC-3), November Pages 141-152; Haralick, R., (1979), Statistical and Structural Approaches to Texture, *Proc. of IEEE*,(67), May, Pages 786-804.) and the neighboring gray-level dependence (NGLD) matrix (See: Sun, C., Wee, W., (1982), Neighboring Gray Level Dependence Matrix for Texture Classification, *Computer Vision Graphics and Image Processing*, (23), Pages 341-352.)

In general, the GLC matrix is based upon the average spatial relationship that gray-tones in an image have to one another, i.e., cooccurence. The underlying assumption is that texture information can be adequately specified by a set of gray tone spatial-dependence matrices that are computed based various pixel differences and orientations. These gray-level co-occurrence matrices are estimates of the second-order joint conditional probability density functions, $p(i,j,d,o)$ and are typically calculated at 4 orientations of 0, 45, 90, and 135 degrees. Each density function is the probability of going from gray level i to gray level j, given that the intersample spacing is d and the direction is given by angle o. If an image has $N_g$ gray levels, then the gray-level cooccurrence matrix is $N_g \times N_g$.

In the example given, all textural features are extracted from the these matrices that were computed from 32×32 pixel samples. For the example, d=1-3 and the features extracted are energy, contrast, correlation, local homogeneity, and entropy.

A limitation of the GLC matrix method is that the matrix and corresponding features must be computed 4 times, once for each orientation. The NGLD method overcomes this limitation by considering the relationship between a pixel and all of its neighbors at one time instead of in one direction at a time. This removes the angular dependency, facilitates invariance under linear gray-level transformations, and reduces the computational load.

The NGLD matrix is formed from the gray-tone relationship between every element in the image and all of its neighbors at a particular distance d. All texture features are then obtained from this NGLD matrix. The matrix is of size $N_g \times N_n$ where $N_g$ is the number of possible gray levels and $N_n$ is the number of possible neighbors. It can be considered as frequency counts of grayness variation of an image and is similar in meaning as a histogram of an image. In the example given, the following features were used, small number emphasis, large number emphasis, number nonuniformity, second moment, and entropy.

Figure 15:
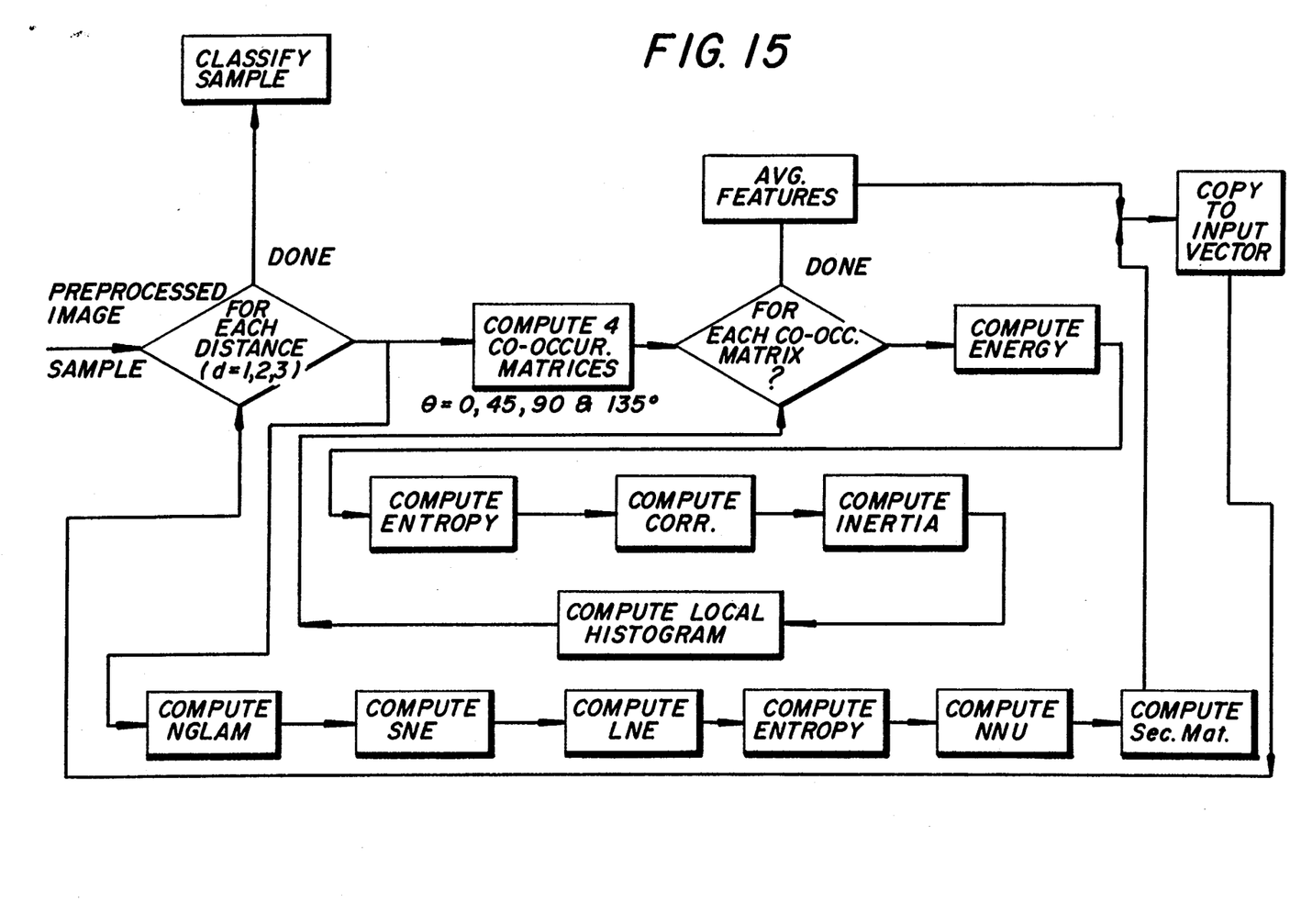
FIG. 15 if a flow chart useful in carrying out the texture feature extraction step.

Referring to FIG. 15, there is shown a software routine for use in the feature extraction step.

Prior to classifying a sample, a neural network classifier was trained on known data (bone, soft tissue, background, foreground samples preprocessed as described above and texture features computed) which was manually hand-selected from a library of radiographic images. (See: U.S. Pat. No. 5,048,097, issued Sep. 10, 1991, Inventors Gaborski et al.)

The learning process is as follows:

Goal: To train a classifier to recognize an unknown sample (never seen before) as one of four classes, i.e., bone, tissue, background, foreground.

Procedure: Collect thousands of samples over a wide range of exams and image conditions which will serve as representative sampling of the entire population of possible samples to be seen under operating conditions. As each sample is selected, a label is affixed to it indicating the appropriate class, i.e., bone, tissue, background, foreground.

Each sample is preprocessed using the identical method to be employed under operating conditions.

Compute texture features referred to above, normalize, and form input vector.

Set up output vector.

e.g.

Bone would map as {1, 0, 0, 0}
Tissue would map as {0, 1, 0, 0}
Bgrd. would map as {0, 0, 1, 0}
Fgrd. would map as {0, 0, 0, 1}

Figure 16:
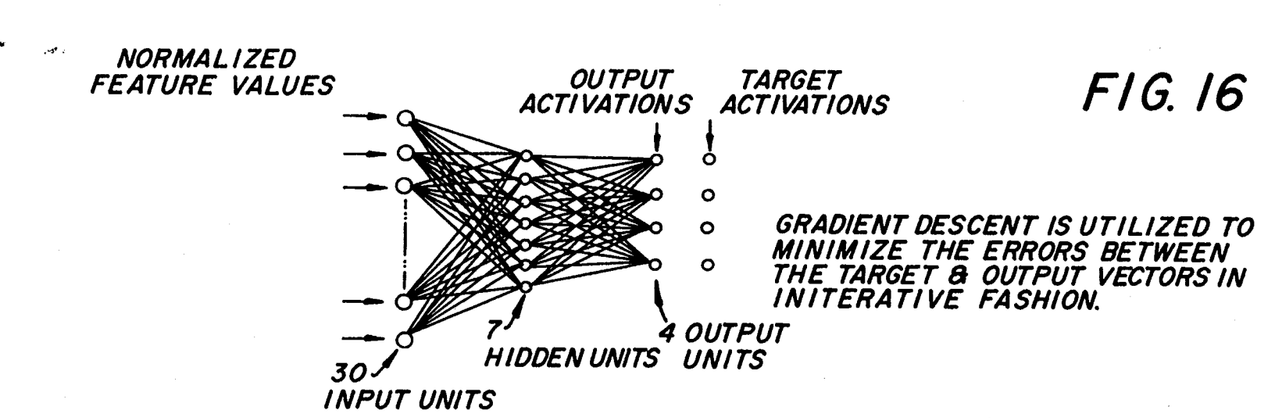
FIG. 16 is a diagrammatic view illustrating a neural network classifier.

These pairs of input and output vectors are then presented to a supervised learning algorithm. The preferred embodiment is a three-layer globally connected neural network. Backward error propagation is the preferred learning algorithm which utilizes gradient descent. Gradient descent is utilized to minimize the errors between the target and output vectors in an iterative fashion. FIG. 16 shows a diagram illustrating a neural network classifier.

Figure 17A:
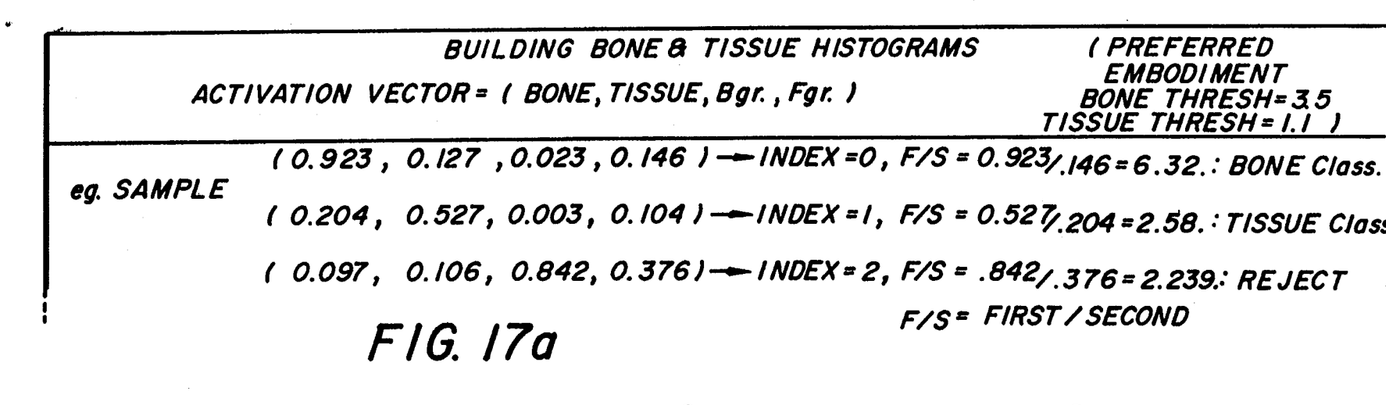
FIGS. 17a and 17b are respectively an example and a flow diagram illustrating the building histogram step.
Figure 17B:
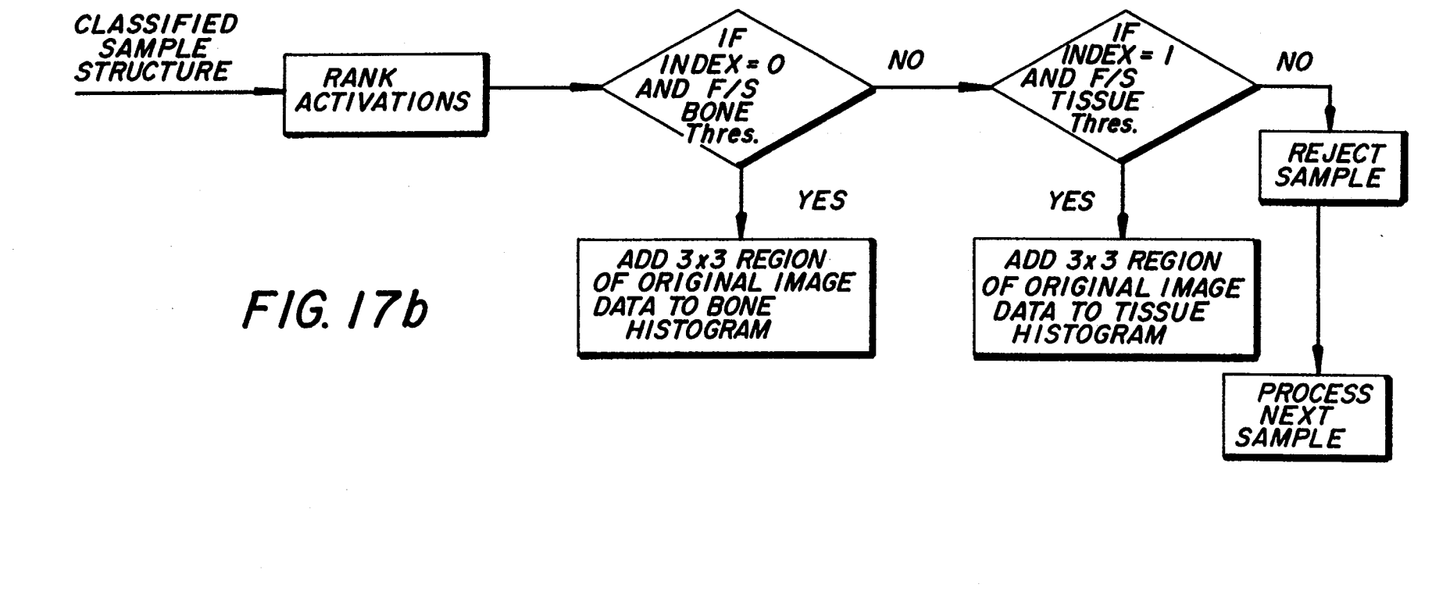
Figure 18:
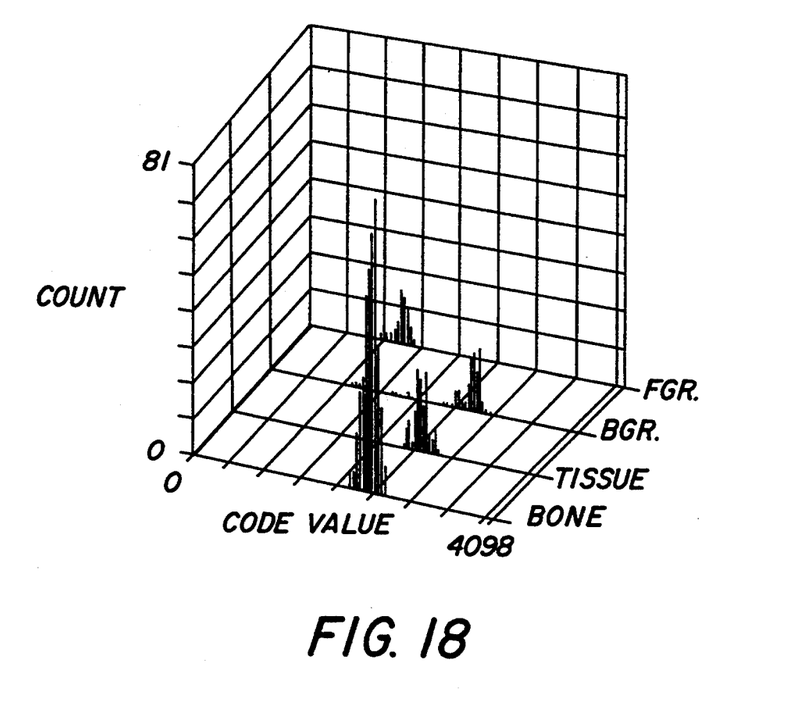
FIGS. 18-23 are graphical views useful in explaining the present invention.

As shown in FIG. 4, the next step is to classify the samples using the previously trained neural network classifier (Box 42). If a sample is found to be of type bone, the central pixel and its surrounding neighborhood (typically 3×3) are all classified as bone and the corresponding pixel data is accumulated with other bone pixel values to build a bone histogram. (Box 44, FIG. 4). The same is done for the other three classes. FIGS. 17a and 17b are respectively an example of histogram building and a software routine for carrying out histogram building. FIG. 18 is a three dimensional graphical view illustrating the histograms built for the four classes described above.

Figure 19:
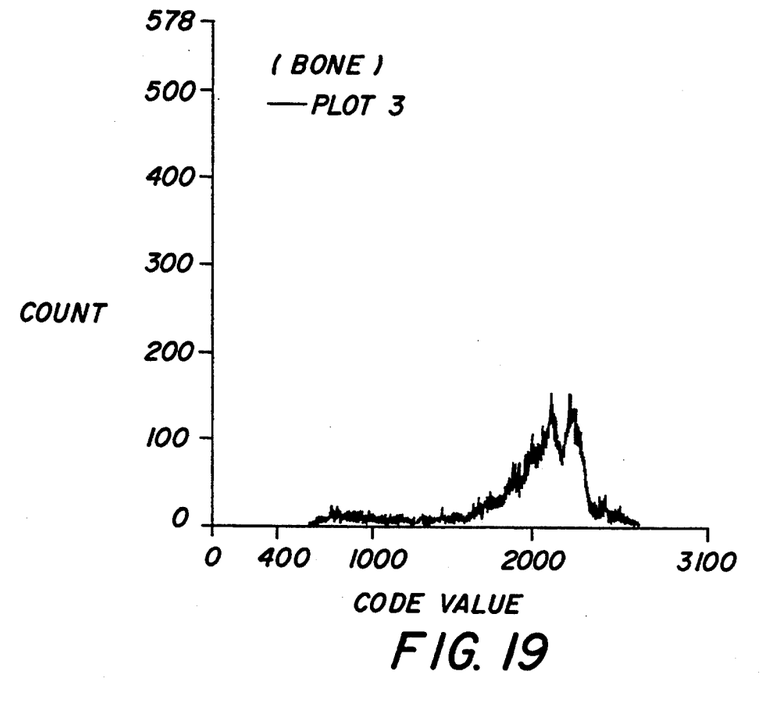
Figure 20:
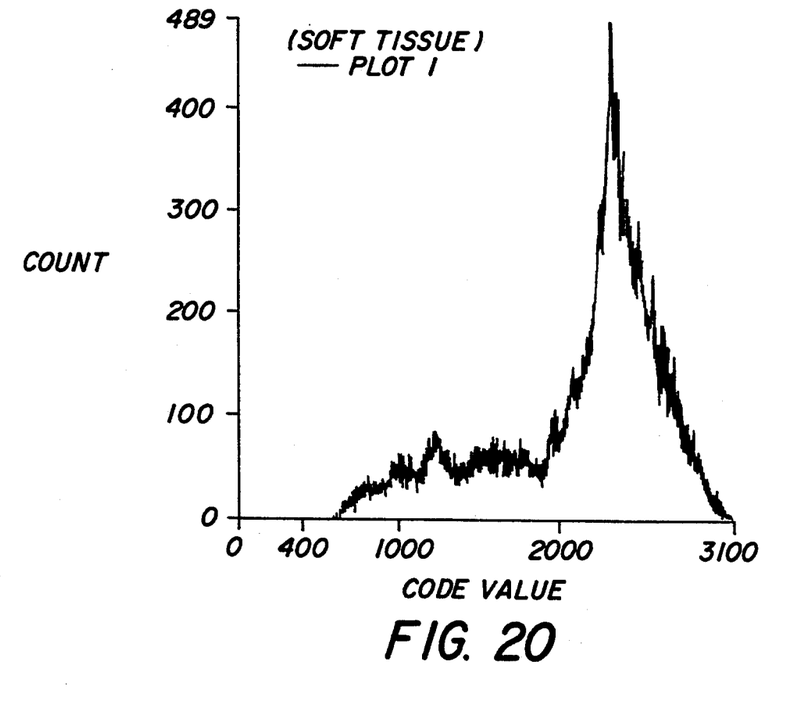
Figure 21:
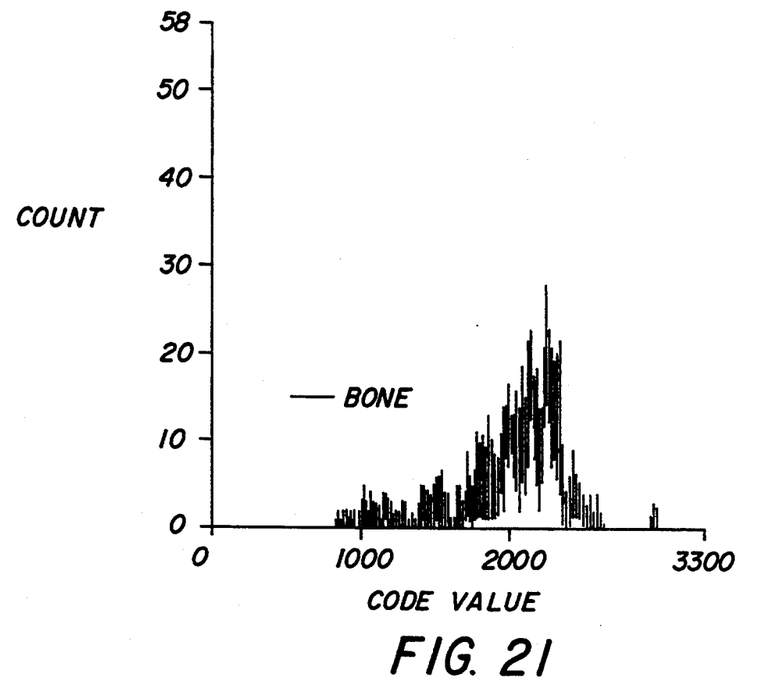
Figure 22:
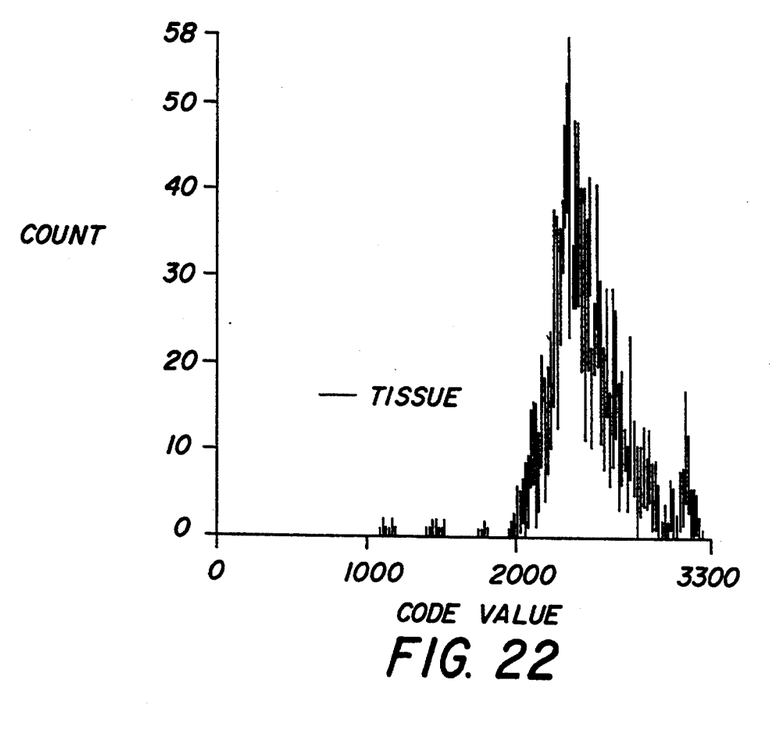

The success of the classification technique of the present invention in more accurately identifying the histograms relating to specific classes is shown in FIGS. 19–22. FIGS. 19 and 20 are actual histograms, respectively, of bone and tissue samples. FIGS. 21 and 22 are histograms, respectively, of bone and tissue sample as classified by the technique of the present invention. The correlation between the actual histograms and the computed histograms is evident.

Figure 23:
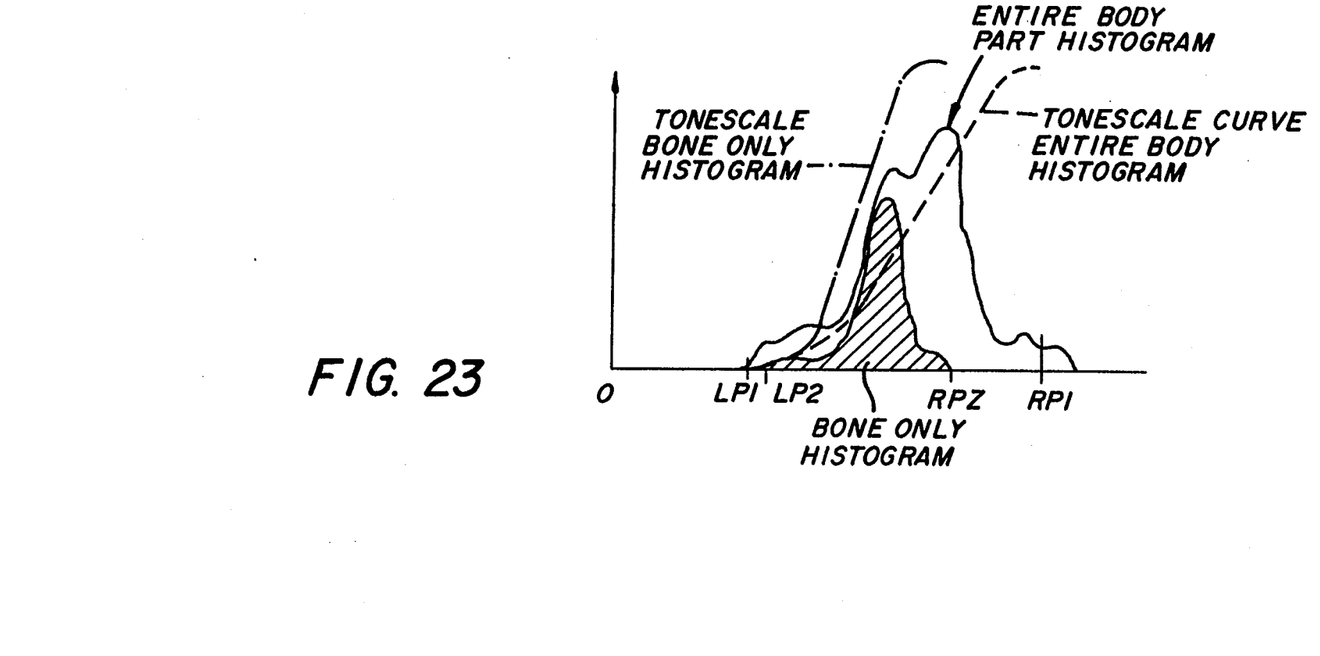

FIG. 23 illustrates the entire body part histogram and the tone scale curve based on it, as well as the bone only histogram and the tonescale curve based on it. Not knowing the bone region, one must make guesses about the left point and especially the right point using the tonescale algorithm of U.S. Pat. No. 5,164,993, referred to above. A wrong decision results in reduced contrast and inconsistency in image presentation. Knowing the limits of the bone and tissue regions enables accurate selection of the left and right points and results in consistency in image presentation.

ADVANTAGES

The advantage of using this technique is that accurate approximations of the various distributions, particularly bone and soft tissue, can be obtained in an automatic fashion without having to develop a complex rule based system that has to analyze every pixel within the image. Development of such a system is time consuming and fault intolerant. A second advantage of this system is that it facilitates customizing to the viewer. For example, if the radiologist is looking for a bone tumor, he might choose to use all of the dynamic range of the tone scale within the bone region and not use any for soft tissue or background. Or for a fracture, he may choose up to 20% of the dynamic range to examine the soft tissue for swelling and 80% for the bone in order to locate the fracture. Another advantage is that if the segmentation stage results in an error such that regions of background or foreground are included in the segmentation mask, the histogram analysis method fails. However, when the histogram is decomposed using texture features, this problem is overcome.

Although the invention has been described with reference to preferred embodiments thereof, it will be understood that variations and modifications can be effected within the spirit and scope of the invention as described above and as defined in the appended claims.

What is claimed is:

1. A method of finding a histogram region of interest for improved tone scale reproduction of digital radiographic images comprising the steps of:
    pseudo-randomly sampling a digital radiographic image with a sample having an appropriate size to delineate a region of interest;
    processing each sample using texture analysis techniques to extract a plurality of texture features;
    using the extracted texture features, classifying said sample with a previously trained neural network classifier to determine its class; and
    accumulating pixel values belonging to the same class to form separate histograms for each said class, wherein each said histogram can be used to optimize tone scale reproduction.

2. The method of claim 1 including the step of segmenting said digital radiographic image into a background region, a foreground region, and an object region of interest, and wherein said sampling step is performed on said object region of interest.

3. The method of claim 1 wherein said sampling step includes a linear pixel shuffling technique.

4. The method of claim 1 wherein, before said processing step, each said sample is preprocessed by reducing the digital value of each sample pixel, and performing an adaptive histogram equalization operation on each said sample, and wherein said processing step is performed on the central region of said preprocessed sample.

5. The method of claim 1 wherein said processing step is performed using a gray-level co-occurrence matrix texture analysis technique to extract a first set of texture features, and also using a neighboring gray-level dependence matrix texture analysis technique to extract a second set of texture features, and wherein said classifying step is performed using said first and said second sets of texture features.

6. The method of claim 5 wherein said first set of texture features include energy, contrast, correlation, local homogeneity, and entropy, and wherein said second set of texture features include small number emphasis, large number emphasis, number nonuniformity, second moment, and entropy.

7. The method of claim 6 wherein said first and second sets of features are determined at intersample distances of 1, 2, and 3, such that each set of features include at least fifteen features, and wherein said thirty features are used in said neural network classifier of said classifying step.

8. The method of claim 1 wherein the histograms of one or more classes can be selectively manipulated to change the tonescale reproduction of said one or more classes.

9. The method of claim 8 wherein said histograms are of one or more body regions of interest and the tonescales of said one or more body regions can be selectively changed to emphasize said on or more body regions of interest.

* * * * *